United States Patent [19]

Goebel

[11] 4,301,364
[45] Nov. 17, 1981

[54] X-RAY DIFFRACTOMETER WITH HIGH TIME RESOLUTION

[75] Inventor: Herbert Goebel, Munich, Fed. Rep. of Germany

[73] Assignee: Siemens Aktiengesellschaft, Berlin & Munich, Fed. Rep. of Germany

[21] Appl. No.: 123,347

[22] Filed: Feb. 21, 1980

[30] Foreign Application Priority Data

Mar. 1, 1979 [DE] Fed. Rep. of Germany ....... 2907948

[51] Int. Cl.³ .................... G01B 15/06; G01N 23/207
[52] U.S. Cl. .................................................. 250/272
[58] Field of Search ................ 250/272, 273, 274, 275

[56] References Cited

U.S. PATENT DOCUMENTS 4,131,794 12/1978 Bruninx ............................... 250/272
4,144,450 3/1979 Goebel ................................ 250/272

Primary Examiner—Davis L. Willis
Assistant Examiner—T. N. Grigsby

Attorney, Agent, or Firm—Hill, Van Santen, Steadman, Chiara & Simpson

[57] ABSTRACT

An x-ray diffractometer is disclosed having a position-sensitive detector which is quasi-continuously movable in stepped fashion around a sample by a stepping motor. Output signals triggered by x-ray quanta are output from the position-sensitive detector and converted by an electronic evaluation unit into a time duration corresponding to a position of a particular x-ray quantum in the detector. The time-digital converter connected to the evaluation unit converts the time duration to a digital signal. A digital adder is provided having three inputs. The first input connects to an output of the time-digital converter, the second input connects to receive a digital value generated by a counter associated with the stepping motor, and a third input connects with a digital region selector. An output of the adder connects to a multi-channel analyzer having a plurality of regions therein for analyzing various desired measurement applications. The digital region selector addresses the appropriate region in the analyzer for a desired measurement application.

4 Claims, 1 Drawing Figure

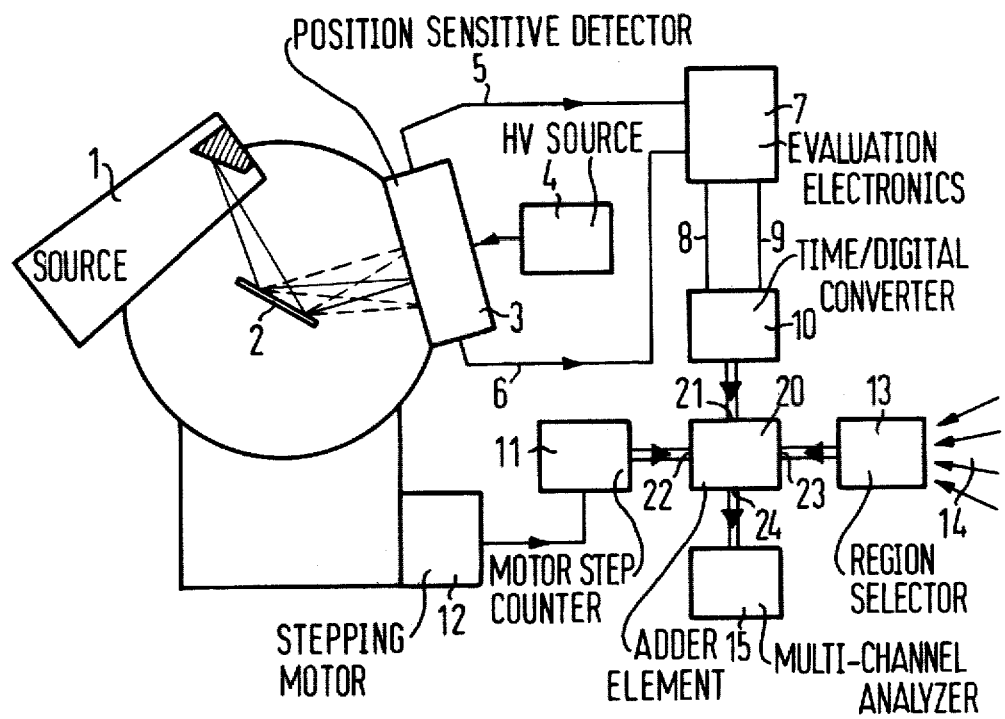

X-RAY DIFFRACTOMETER WITH HIGH TIME RESOLUTION

BACKGROUND OF THE INVENTION

The invention relates to an x-ray diffractometer with a position-sensitive detector which is movable in stepped fashion around a sample and which generates output signals triggered by each x-ray quantum. An electronic evaluation unit converts the output signals into a time duration corresponding to a position of a particular x-ray quantum in the detector. A time-digital converter converts the time duration to a digital signal and the digital signal is combined with another digital signal corresponding to a position of the dectector determined by the stepping motor.

Such x-ray diffractometers are known, for example, from German AS No. 2637945, incorporated herein by reference, for rapid measurement over a large angle range. The possibilities of the position-sensitive detector to simultaneously cover a plurality of angular degrees of the measuring circle without thereby losing resolution, are advantageously exploited in a simple manner for x-ray diffractometers. In this manner, the measuring time has already been reduced to approximately 1/100 of the traditional systems, i.e. systems without position-sensitive detectors.

For covering a larger angle range, the detector in the known x-ray diffractometer is moved by means of a stepping motor. The motor steps are added in a counter. The counting result-after a demultiplication, if necessary-represents the digital value for the detector position and more precisely for the center of the detector. A time-digital transducer supplies the deviation from the detector center for every x-ray quantum registered in the detector. The respective sum of these two values corresponds to the exact angular attitude of the registered x-ray quantum and determines the address in a multi-channel analyzer at which this event is stored.

In many investigations, it also suffices to only observe a limited angular range. Such uses, for example, can be phase transitions under pressure or high and low temperatures, domain collapsing processes, solid state reactions, formation processes, expansion measurements, voltage measurements, and the like. In particular, the dynamics of such processes as a function of various measuring parameters is thereby of interest.

SUMMARY OF THE INVENTION

Given an x-ray diffractometer it is therefore an object of the present invention to render possible in a simple manner the dependancy of the perceived diffraction patterns on the measuring parameters in addition to the rapid investigation of large angle ranges. Furthermore, it is also an object to eliminate or at least reduce the errors, for example, in the allocation of the diffraction patterns which may be produced to the addresses of the multi-channel analyzers, said errors being due to the electronic components functioning in a marginal time range.

These objects are inventively achieved in that a digital region selector or change switch is provided whose output is connected to a further input of the digital adder. Simply by means of this single additional component, the range of application of the x-ray diffractometer is significantly increased in the simplest manner. Thus, for example, it becomes possible to switch over the perceived diffraction patterns in succession to any desired regions or areas of the multi-channel analyzer and, by so doing, to register with high time resolution. A different measuring parameter is thereby allocated to each region or area. Given periodic processes, time resolutions of approximately 10 μs can be achieved. Given unique events, measuring times in the magnitude of 0.1 Sec are required because of the necessary counting statistics.

The investigation of such dynamic processes can be undertaken given a stationary x-ray diffractometer in that the output signal of the region selector represents binary addresses which respectively fix or determine a region or area of the multi-channel analyzer, said output signals at the same time corresponding to a measuring parameter. For example, given a multi-channel analyzer with $2^{12}=4096$ channels, one can conceive of this being separated into $2^5=32$ regions of $2^7=128$ channels each. The 32 regions are driven in time succession. To achieve this, 12 bit binary addresses arriving from the region selector are applied to the further summer input. Of these 12 bit binary addresses, the 7 lowest-order bits are set at zero and the bits 8–12 make the region selection.

It is provided in a further development of the invention that the region selector is driven by means of a measuring parameter. For this purpose, one can employ, for example, physical magnitudes such as time, pressure, temperature, electric or magnetic fields which must then be appropriately digitalized. For the example cited, the measuring parameter characteristic for the state of a sample would have to be converted into a 5 bit word.

In a corresponding manner, the 4096 channels, for example, of the multi-channel analyzer can be subdivided into any desired powers of 2 as the product of (region) x (number of regions).

An additional increase of the measuring precision can be advantageously achieved when, in addition to the time region advancing, the position-sensitive detector is moved by a small angle range around its stationary rest position. Any potential errors due to the evaluation electronics are discovered in this manner. Given such a combind measuring method, in which on the one hand, the region selection or spectrum multiscaling is undertaken as a function of specific measuring parameters and the angle range under consideration is periodically changed independently of the measuring parameters, an advantageous embodimemt of the x-ray diffractometer with a digital summer with n-bits provides that the lowest-order m-bits are set to "low" and the highest-order k-bits in the output signal of the region selector (the region selector output signal representing the binary region address) are available for the change to a new region, whereby $m+k \leq n$. By so doing, the gaps remain free between the individual regions fixed by the measuring parameters. As a function of the size of the additional periodic excursion of the detector, these gaps should be selected large enough so that no overlapping occurs between individual regions.

An x-ray diffractometer for the investigation of dynamic processes, for example, of muscle contraction, is already known from the periodical "JAPPL. CRYST." 1978, volume 11, pages 449–454, incorporated herein by reference. The electronic structure as is specified, for example, in figure 4 on page 452 of this publication, however, involves significantly more expense than that according to the invention. Instead of a simple summer or adder, a control unit for a multi-region selection and an additional interface for conforming to the multi-channel analyzer are required.

In particular, however, it is not possible with the x-ray diffractometer known from this publication to switch or change-over between the spectrum multiscaling or the channel selection of the multi-channel analyzer synchronously with the motion of the diffractometer and a region switching or selection as a function of a measuring parameter. A meaningful combination of these two possible applications increasing the measuring precision is likewise not suggested.

BRIEF DESCRIPTION OF THE DRAWING

The drawing FIGURE schematically illustrates an x-ray diffractometer with position-sensitive detector and a block diagram for the drive of a multi-channel analyzer employed in the invention.

DESCRIPTION OF THE PREFERRED EMBODIMENTS

The monochromatic x-ray beam emerging from the source 1 strikes a sample 2. The x-ray beam proceeding from this sample 2 is registered by a position-sensitive detector 3 which is provided with a high-voltage source 4. The detector signals triggered due to each incident x-ray quantum are supplied via two lines 5 and 6 to an evaluation electronics 7 for signal recognition and shaping. The output signals of the evaluation electronics 7 on the lines 8 and 9 indicate the start and stop time for a following time/digital transducer or converter 10. The time difference between start and stop time is a measure for the position of the registered x-ray quantum on the detector 3.

The output of the time/digital transducer or converter 10 is connected to an input 21 of a binary summer or adder element 20. A further input 22 of this summer or adder element 20 is connected to the output of a motor step counter 11 which sums the forward and backward steps of a stepping motor 12. The stepping motor 12 serves for the movement of the entire detector 3. In digital form, the output value of the motor step counter 11 indicates the position of the center of the position-sensitive detector 3. The adder or summer element 20 exhibits an additional input 23 which is connected to the output of a digital region selector or change-over switch 13. This digital region selector 13—as indicated by means of arrows 14—can be driven by means of widely varying types of measuring parameters such as time, temperature, pressure or electrical measured values. The output 24 of the summing element 20 serves for the address selection of a multi-channel analyzer 15.

With the assistance of this simple adder element 20 with its three inputs, the x-ray diffractometer is suitable for widely varying types of use. By means of the addition of the digital signals of the motor step counter 11 and of the time/digital transducer or converter 10, one obtains the exact angular attitude for each registered quantum. Given a quasi-continuous rotation of the detector 3 with the assistance of the stepping motor 12, it is thus possible to quickly cover a large angle range.

If, on the other hand, dynamic operations are to be investigated in a sample and if a small angular range suffices for this, then given a stationary detector 3, it can be achieved via the region selector 13 driven by a measuring parameter that the perceived diffraction patterns are switched in succession to different regions of the multi-channel analyzer 15. A different measuring parameter is thereby allocated to each of these regions. It is possible in this manner to investigate dynamic processes in the sample with high time resolution.

A further field of application results when the dynamic processes do not occur too quickly. In this case, the covered angular range which, given a stationary detector 3, is determined by the angular range of the detector 3, can be simply and advantageously increased in that the detector 3 is periodically moved around a rest position, for example with the assistance of stepping motor 12. Due to the addition of the digital signals at the inputs 21 through 23 of the adder element 20, it is thereby again assured that every x-ray quantum striking detector 3 is, on the one hand, allocated to the appropriate region of the multi-channel analyzer 15 depending on the measuring parameter, and, on the other hand, is stored within this region at the proper address.

The following commercially available units or publication descriptions may be employed for construction of the invention:

adder element 20 and motor step counter 11: Siemens Part #C72298-A223-C253 (Dept. E689)

region selector 13: Reithley 160 digital voltmeter or Hewlett-Packard 5245L counter multichannel analyzer 15: American Canberra Co. Type 8100 MCA evaluation electronics 7 and position sensitive detector 3: Advances in X-ray Analysis, Vol. 22 pages 255-265 (1979); also Siemens Part #7KP6000-8AA (Dept. E689)

time-digital converter 10: Siemens Part #C72298-A223-C254 (Dept. E689)

Although various minor modifications may be suggested by those versed in the art, it should be understood that I wish to enbody within the scope of the patent warranted hereon, all such embodiments as reasonably and properly come within the scope of my contribution to the art.

I claim as my invention:

1. An x-ray diffractometer, comprising: a position-sensitive detector means quasi-continuously movable in stepped fashion around a sample on a predetermined path by a stepping motor, the detector means providing output signals triggered by x-ray quanta; electronic evaluation means for converting the output signals into a time duration corresponding to a position of a particular x-ray quantum in the detector means; a time-digital converter means connected to the evaluation means for converting the time duration to a digital signal; a digital adder means having a first input connected to an output of the time-to-digital converter means and a second input connected to receive a digital value generated by counter means associated with the stepping motor and corresponding to a position of the detector means; a multi-channel analyzer means driven by the adder means and having a plurality of regions for analyzing various desired measurement applications; and a digital region selector means having its output signal connected to a third input of the digital adder means, the selector means selecting a region from the plurality of regions within the analyzer means corresponding to a desired diffractometer measurement application.

2. An x-ray diffractometer according to claim 1 wherein the region selector means is driven by a measuring parameter for a desired measuring application.

3. An x-ray diffractometer according to claim 1 wherein the digital adder means has n bits; and, in the output signal of the region selector representing an address of the desired region, m lowest order bits are set to "low" and k highest-order bits are available for the region selection, whereby $m+k \leqq n$.

4. An x-ray diffractometer, comprising: a position-sensitive detector means moved about a sample by a drive means, the detector means providing output signals triggered by x-ray quanta; electronic evaluation means for converting the output signals into a time duration signal corresponding to a position of a particular x-ray quantum in the detector means; a time-to-digital converter means connected to the evaluation means for converting the time duration to a digital signal; a digital adder means having a first input connected to an output of the time-digital converter means and a second input connected to receive a digital value generated by the drive means which corresponds with a position of the detector means; a multi-channel analyzer means driven by the adder means and having a plurality of regions for analyzing various desired measurement applications; and a digital region selector means having its output signal connected to a third input of the digital adder means, the selector means selecting a region from the plurality of regions within the analyzer means corresponding to a desired diffractometer measurement application.

* * * * *